(12) United States Patent
Taniguchi et al.

(10) Patent No.: US 6,469,210 B1
(45) Date of Patent: Oct. 22, 2002

(54) PROCESS FOR THE PREPARATION OF PHENYLALKANOIC ACID AMIDES AND INTERMEDIATES THEREFOR

(75) Inventors: Shuji Taniguchi; Hidetaka Hiyoshi; Katsunori Matsumoto, all of Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/720,492
(22) PCT Filed: Apr. 27, 2000
(86) PCT No.: PCT/JP00/02774

§ 371 (c)(1),
(2), (4) Date: Dec. 27, 2000

(87) PCT Pub. No.: WO00/66542

PCT Pub. Date: Nov. 9, 2000

(30) Foreign Application Priority Data

Apr. 28, 1999 (JP) ............................................. 11-122930

(51) Int. Cl.[7] ............................................. C07L 233/00
(52) U.S. Cl. ........................ 564/182; 548/228; 562/444; 562/449; 562/450; 564/170
(58) Field of Search ................................. 562/444, 449, 562/450; 564/170, 182; 548/228

(56) References Cited

U.S. PATENT DOCUMENTS 4,264,771 A  *  4/1981  Steglich

FOREIGN PATENT DOCUMENTS

| EP | 0 854 134 A1 | 5/1996 |
| EP | 0 816 330 A1 | 6/1997 |
| JP | 53-84967 | * 7/1978 |
| WO | WO-95/12573 | * 5/1995 |

* cited by examiner

Primary Examiner—Michael L. Shippen
(74) Attorney, Agent, or Firm—Kubovcik & Kubovcik

(57) ABSTRACT

A process for producing a phenylalkanoic acid amide of the formula [3]

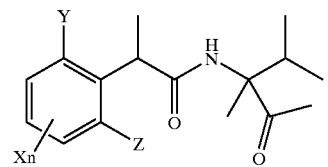

by reacting a carboxylic acid of the formula [1]

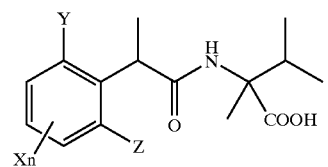

with a dehydrating agent to produce an oxazolinone compound of the formula [2]

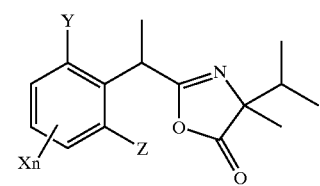

and then reacting the oxazolinone compound with methyllithium or a methylmagnesium halide and an intermediate for producing the phenylalkanoic acid compound.

7 Claims, No Drawings

PROCESS FOR THE PREPARATION OF PHENYLALKANOIC ACID AMIDES AND INTERMEDIATES THEREFOR

TECHNICAL FIELD

The present invention relates to a process for producing a phenylalkanoic acid amide compound and an intermediate for producing the compound.

BACKGROUND ART

Some of the phenylalkanoic acid amides are known to be useful as an effective ingredient for fungicide (for example, JP-A-9-48750 and Japanese Patent Application No. 10-296078); however, no process is known for producing such a phenylalkanoic acid amide compound from an oxazolinone compound.

The present invention aims at providing a process for simple and easy production of a phenylalkanoic acid amide compound having an excellent fungicidal activity.

DISCLOSURE OF THE INVENTION

The present inventor made a hard study zealously in order to solve the above subject. As a result, the present inventor found out that the intended phenylalkanoic acid amide compound can be produced by reacting an oxazolinone compound with methyllithium or a methylmagnesium halide and the above aim can be achieved. The present invention has been completed based on the above finding.

BEST MODE FOR CARRYING OUT THE INVENTION

The present invention is described in detail below.

The above aim of the present invention has been achieved by providing the inventions shown in the following [1] to [8].

[1] A process for producing a phenylalkanoic acid amide represented by the following general formula [3]

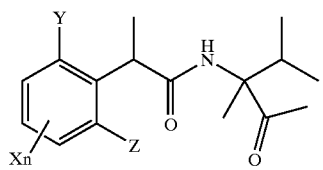

[3]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom or the like), which process comprises reacting a carboxylic acid compound represented by the following general formula [1]

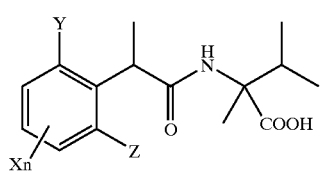

[1]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) with a dehydrating agent to produce an oxazolinone compound represented by the following general formula [2]

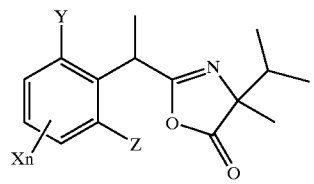

[2]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) and then reacting the oxazolinone compound with methyllithium or a methylmagnesium halide.

[2] A carboxylic acid compound represented by the following general formula [1]

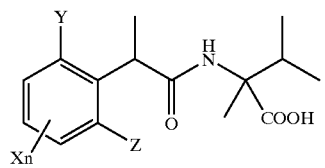

[1]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom).

[3] An oxazolinone compound represented by the following general formula [2]

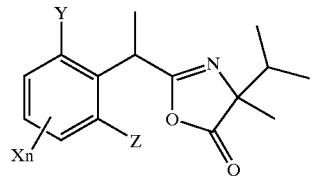

[2]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom).

[4] A process for producing an oxazolinone compound represented by the following general formula [2]

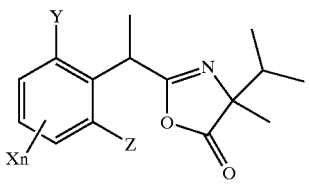

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom), which process comprises reacting a carboxylic acid compound represented by the following general formula [1]

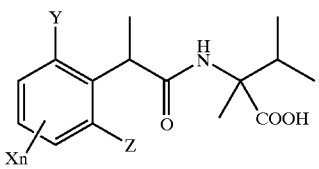

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) with a dehydrating agent.

[5] A process for producing a phenylalkanoic acid amide represented by the following general formula [3]

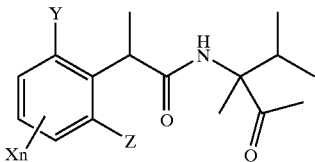

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom, a hydrogen atom or the like), which process comprises reacting an oxazolinone compound represented by the following general formula [2]

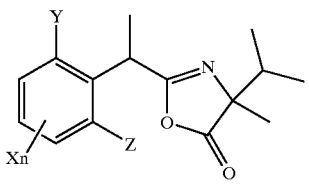

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom, a hydrogen atom or the like) with methyllithium or a methylmagnesium halide.

[6] A process for producing a phenylalkanoic acid amide, set forth in the above [1], wherein the dehydrating agent is an acid anhydride, a thionyl halide compound, a phosphorus halide compound or a halocarbonic acid ester compound.

[7] A process for producing a phenylalkanoic acid amide, set forth in the above [1], wherein the methylmagnesium halide is methylmagnesium chloride or methylmagnesium bromide.

[8] A process for producing a phenylalkanoic acid amide, set forth in the above [1], wherein the dehydrating agent is an acid anhydride, a thionyl halide compound, a phosphorus halide compound or a halocarbonic acid ester compound and the methylmagnesium halide is methylmagnesium chloride or methylmagnesium bromide.

The present invention is described in detail below.

The process of the present invention described in the above [1] is constituted by a step of reacting a carboxylic acid compound represented by the above general formula [1] (which is the present invention compound described in the above [2]) with a dehydrating agent to give rise to intramolecular ring closure to produce an oxazolinone compound represented by the general formula [2] (which is the present invention compound described in the above [3]) (this step is referred to as step 1 and corresponds to the present invention process described in the above [4]) and a step of reacting the oxazolinone compound represented by the general formula [2] with methyllithium or a methylmagnesium halide to give rise to ring opening of oxazolinone ring to produce a phenylalkanoic acid amide compound represented by the general formula [3] which is an intended final product (this step is referred to as step 2 and corresponds to the present invention process described in the above [5]).

Description is made first on the production of a carboxylic acid compound represented by the general formula [1], which is used as a raw material in the step 1 of the present invention process. The carboxylic acid compound represented by the general formula [1] is a novel compound and is useful as a raw material used in production of the oxazolinone compound represented by the general formula [2], which is an intended compound in the step 1.

The carboxylic acid compound represented by the general formula [1], used in the present invention can be produced by reacting an ester compound represented by the following general formula [4], with an acid or a base in the presence of water to hydrolyze the ester moiety of the ester compound.

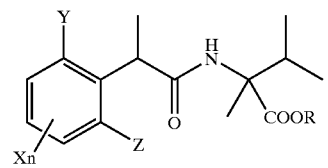

In the above formula [4], R is a straight chain or branched chain alkyl group of 1 to 6 carbon atoms (hereinafter, carbon atoms are abbreviated to, for example, C1 to C6 in the case of 1 to 6 carbon atoms), such as methyl group, ethyl group, n-propyl group, isopropyl group, n-butyl group, sec-butyl group, tert-butyl group, n-pentyl group, n-hexyl group or the like; a C3 to C6 cycloalkyl group such as cyclopropyl group, cyclobutyl group, cyclopentyl group, cyclohexyl group or the like; a straight chain or branched chain C1 to C6 haloalkyl group such as chloromethyl group, trifluoromethyl group or the like; an aryl group such as phenyl group, naphthyl group or the like; a halogen-, C1 to C6 alkyl- or C1 to C6 alkoxy-substituted aryl group such as 4-chlorophenyl group, 2-methylphenyl group, 4-mehtoxyphenyl group or the like; an aralkyl group such as benzyl group or the like, or a halogen-, C1 to C6 alkyl- or C1 to C6 alkoxy-substituted aralkyl group such as 4-chlorobenzyl group, 4-methylbenzyl group, 4-methoxybenzyl group or the like, X is a hydrogen atom; a straight chain or branched chain C1 to C6 alkyl group such as methyl group, ethyl group, n-propyl group, isopropyl group, n-butyl group, sec-butyl group, tert-butyl group, n-pentyl group, n-hexyl group or the like; a straight chain or branched chain C1 to C6 alkoxy group such as methoxy group, ethoxy group, propyloxy group or the like; a straight chain or branched chain C1 to C6 haloalkyl group such as chloromethyl group, trifluoromethyl group or the like, or a halogen atom such as fluorine atom, chlorine atom, bromine atom or the like, n is an integer of 1 to 3 and when n is 2 or more, a plurality of Xs may be the same or different, and Y and Z are each independently a halogen atom such as fluorine atom, chlorine atom, bromine atom or the like, or a hydrogen atom.

As specific examples of the ester compound having such substituents, represented by the general formula [4], there can be exemplified methyl 2-[2-(4-chlorophenyl)-propanoylamino]-2,3-dimethylbutanoate, methyl 2-[2-(2,4-di-chlorophenyl)propanoylamino]-2,3-dimethylbutanoate, methyl 2-[2-(4-fluorophenyl)propanoylamino]-2,3-dimethylbutanoate, methyl 2-[2-(4-bromophenyl) propanoylamino]-2,3-dimethylbutanoate, methyl 2-[2-(4-iodophenyl)propanoylamino]-2,3-dimethylbutanonate, phenyl 2-[2-(3,4-dichlorophenyl)propanoylamino]-2,3-dimethylbutanonate, benzyl 2-[2-(4-methylphenyl) propanoylamino]-2,3-dimethylbutanonate, methyl 2-[2-(4-methoxyphenyl)propanoylamino]-2,3-dimethylbutanoate, methyl 2-[2-(2-chlorophenyl)propanoylamino]-2,3-dimethylbutanonate and methyl 2-[2-(2,6-dichlorophenyl) propanoylamino]-2,3-dimethylbutanonate.

The hydrolysis is conducted by using an acid or a base, in the presence of water of an amount of 1 mole or more relative to 1 mole of the ester compound represented by the general formula [4].

The acid usable in the hydrolysis can be exemplified by mineral acids such as sulfuric acid, hydrochloric acid and the like. The base usable in the hydrolysis can be exemplified by alkali metal hydroxides such as sodium hydroxide, potassium hydroxide and the like, and alkali metal carbonates such as potassium carbonate, sodium carbonate and the like. The hydrolysis is preferably carried out by using an alkali metal hydroxide typified by sodium hydroxide. There is no particular restriction as to the amount of the acid or the base used as long as the amount can cause the hydrolysis of ester linkage but causes no hydrolysis of amide linkage. However, the amount can be, for example, 0.001 to 5 moles, preferably 0.05 to 2 moles per 1 mole of the ester compound represented by the general formula [4].

The hydrolysis is ordinarily conducted using a solvent. As the solvent, there can be mentioned, for example, aromatic hydrocarbons such as toluene, xylene, chlorobenzene and the like; acetic acid esters such as methyl acetate, ethyl acetate, butyl acetate and the like; aprotic polar solvents such as dimethylformamide, dimethylacetamide, dimethyl sulfoxide and the like; ether type solvents such as diethyl ether, tetrahydrofuran, dioxane, monoglyme, diglyme and the like; aliphatic hydrocarbons such as pentane, n-hexane and the like; nitriles such as acetonitrile and the like; ketones such as acetone, methyl ethyl ketone, methyl isobutyl ketone and the like; polyethylene glycols such as polyethylene glycol 400 (PEG 400) and the like; and water. These solvents can be used singly or as a mixed solvent consisting of any proportions of two of more solvents. The amount of the solvent used can be any if it can assure thorough stirring; however, it is, for example, 0.5 to 5 liters, preferably 1 to 3 liters per 1 mole of the ester compound represented by the general formula [4].

The temperature of the hydrolysis can be, for example, 0° C. to the reflux temperature of the solvent used and is preferably 0 to 80° C.

As to the time of the hydrolysis, there is no particular restriction; however, the time is preferably 0.5 to 6 hours.

The ester compound represented by the general formula [4] is a publicly known compound, or can be produced by a known method which comprises condensing a known corresponding amino acid ester with a corresponding acid chloride, or a method which comprises reacting a nitrile compound represented by the following general formula

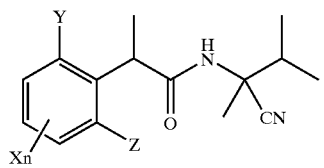

(wherein X, Y, Z and n each have the same definition as given previously) with an alcohol. The nitrile compound represented by the above general formula is a publicly known compound, or can be produced by a method which comprises condensing a known corresponding carboxylic acid with a corresponding amino-nitrile compound.

In Table 1 are shown specific examples of the carboxylic acid compound of the present invention represented by the general formula [1], which is used as a raw material in the step 1 of the present invention process. The carboxylic acid compound of the present invention, however, is not restricted to them and includes all of the compounds represented by the general formula [1]. Here, the X, Y, Z and n in the general formula [1] each have the same definition as in the general formula [4]. The carboxylic acid compound of the present invention includes those which have one or more asymmetric carbon atom(s) and which are an enantiomer or a diastereomer. The carboxylic acid compound of the present invention includes all of such isomers per se and mixtures (e.g. racemic modifications) of any proportions of isomers. In Table 1, refractive index ($n_D^{20}$) is a value obtained by measurement at 20° C. using a Na-D line.

TABLE 1

| No. of compound | Xn | Y | Z | Melting point (° C.) or refractive index ($n_D^{20}$) |
|---|---|---|---|---|
| 1-1 | 4-Cl | H | H | 128–137 |
| 1-2 | 4-Cl | Cl | H | |
| 1-3 | 4-F | H | H | |
| 1-4 | 4-Br | H | H | |
| 1-5 | 4-I | H | H | |
| 1-6 | 3,4-Cl$_2$ | H | H | |
| 1-7 | 4-CF$_3$ | H | H | |
| 1-8 | 4-CF$_3$ | H | H | |
| 1-9 | 4-OCH$_3$ | H | H | |
| 1-10 | H | Cl | H | |
| 1-11 | H | Cl | Cl | |

Next, description is made on the reaction of the step 1 of the present invention process. In the step 1 of the present invention process, the carboxylic acid compound represented by the general formula [1] is reacted with a dehydrating agent to produce an oxazolinone compound represented by the general formula [2].

As the dehydrating agent used in the step 1 of the present invention process, there can be mentioned, for example, acid anhydrides such as acetic anhydride and the like; thionyl halide compounds such as thionyl chloride and the like; phosphorus halide compounds such as phosphorus oxychloride, phosphorus pentachloride and the like; and halocarbonic acid ester compounds such as methyl chlorocarbonate and the like. However, an acid anhydride typified by acetic anhydride is used preferably. The amount of the dehydrating agent used can be such that causes no decomposition of the oxazolinone compound represented by the general formula [2] formed, and can be, for example, 1 to 5 moles, preferably 1 to 2 moles per 1 mole of the carboxylic acid compound represented by the general formula [1].

The reaction of the step 1 can be conducted sufficiently even in the absence of any solvent, but may also be conducted in the presence of a solvent. The solvent may be any solvent which does not impair the reaction, and there can be used, for example, aromatic hydrocarbons such as toluene, xylene, chlorobenzene and the like; acetic acid esters such as methyl acetate, ethyl acetate, butyl acetate and the like; aprotic polar solvents such as dimethylformamide, dimethylacetamide and the like; ether type solvents such as diethyl ether, tetrahydrofuran, dioxane, monoglyme, diglyme and the like; aliphatic hydrocarbons such as pentane, n-hexane and the like; nitrites such as acetonitrile and the like; ketones such as acetone, methyl ethyl ketone, methyl isobutyl ketone and the like; and polyethylene glycols such as polyethylene glycol 400 (PEG 400) and the like. These solvents can be used singly or as a mixed solvent consisting of any proportions of two or more solvents. The amount of the solvent used can be any if it can assure thorough stirring; however, it can be, for example, 0.5 to 5 liters, preferably 1 to 2 liters per 1 mole of the carboxylic acid compound represented by the general formula [1].

The reaction temperature of the step 1 is 0° C. to the reflux temperature of the solvent used, but is preferably 0 to 120° C.

As to the reaction time, there is no particular restriction, but 0.3 to 6 hours are preferred.

The oxazolinone compound represented by the general formula [2], obtained in the step 1 is a novel compound and is useful as an intermediate for phenylalkanoic acid amide compound known to be useful as a fungicide.

In Table 2 are shown specific examples of the oxazolinone compound of the present invention represented by the general formula [2]. The oxazolinone compound of the present invention is not restricted to them and includes all of the compounds represented by the general formula [2]. Here, the X, Y, Z and n in the general formula [2] each have the same definition as in the general formula [4]. The oxazolinone compound of the present invention includes those which have one or more asymmetric carbon atom(s) and which are an enantiomer or a diastereomer. The oxazolinone compound of the present invention includes all of such isomers per se and mixtures (e.g. racemic modifications) of any proportions of isomers. In Table 2, refractive index ($n_D^{20}$) is a value obtained by measurement at 20° C. using a Na-D line.

TABLE 2

| No. of compound | Xn | Y | Z | Melting point (° C.) or refractive index ($n_D^{20}$) |
|---|---|---|---|---|
| 2-1 | 4-Cl | H | H | 1.5129 |
| 2-2 | 4-Cl | Cl | H | |

TABLE 2-continued

| No. of compound | Xn | Y | Z | Melting point (° C.) or refractive index ($n_D^{20}$) |
|---|---|---|---|---|
| 2-3 | 4-F | H | H | |
| 2-4 | 4-Br | H | H | |
| 2-5 | 4-I | H | H | |
| 2-6 | 3,4-Cl$_2$ | H | H | |
| 2-7 | 4-CF$_3$ | H | H | |
| 2-8 | 4-CH$_3$ | H | H | |
| 2-9 | 4-OCH$_3$ | H | H | |
| 2-10 | H | Cl | H | |
| 2-11 | H | Cl | Cl | |

In the step 2 of the present invention process, the oxazolinone compound represented by the general formula [2] is reacted with methyllithium or a methylmagnesium halide to give rise to ring opening of oxazolinone ring, whereby is produced a phenylalkanoic acid amide compound represented by the general formula [3] which is an intended final product.

As the methyllithium or methylmagnesium halide used in the step 2 of the present invention process, there can be mentioned, for example, methyllithium and methylmagnesium halides (methyl Grignard reagents) such as methylmagnesium chloride, methylmagnesium bromide and the like. The amount of the methyllithium or methylmagnesium halide used is not restricted if it does not impair the reaction of the step 2; however, it can be, for example, 0.5 to 3 moles, preferably 1 to 2 moles per 1 mole of the oxazolinone compound represented by the general formula [2].

The ring opening reaction is conducted ordinarily in a solvent. As the solvent, there can be mentioned, for example, ethers such as tetrahydrofuran, diethyl ether, dioxane, monoglyme and the like; aromatic hydrocarbons such as toluene, xylene, chlorobenzene and the like; aprotic polar solvents such as dimethylformamide, dimethylacetamide and the like; aliphatic hydrocarbons such as pentane, n-hexane and the like; pyridines such as pyridine and the like; and polyethylene glycols such as polyethylene glycol 400 (PEG 400) and the like. These solvents can be used singly or as a mixed solvent consisting of any proportions of two of more solvents. Tetrahydrofuran per se or a mixed solvent consisting of tetrahydrofuran and xylene is preferred. The amount of the solvent used can be any if it can assure stirring; however, it can be, for example, 0.5 to 5 liters, preferably 1 to 3 liters per 1 mole of the oxazolinone compound represented by the general formula [2].

The temperature of the ring opening reaction can be −78° C. to the reflux temperature of the solvent used. It is preferably −10 to 60° C., for example.

As to the time of the ring opening reaction, there is no particular restriction, but the time is preferably 0.5 to 6 hours.

Next, the process for production of the present invention product is described specifically by way of Examples.

EXAMPLE 1 (Corresponding to the Invention of the Above [1])

Step 1 (Corresponding to the Invention of the Above [4])

Production of 2-[1-(4-Chlorophenyl)ethyl]-4-isopropyl-4-methyl-1,3-oxazol-5-one 3.7 g (12.5 mmol) of 2-[2-(4-chlorophenyl)-propanoylamino]-2,3-dimethylbutanoic acid was suspended in 50 ml of toluene. Thereto was added 2 g (19.6 mmol) of acetic anhydride. The mixture was refluxed with heating, to give rise to a reaction. The reaction was complete in 20 minutes. The reaction mixture was cooled to room temperature. 50 ml of water was added and phase separation was allowed to take place. The separated organic layer was washed with 30 ml of water and 30 ml of a saturated aqueous sodium bicarbonate solution, and then concentrated to obtain 3.2 g (yield=97%) of 2-[1-(4-chlorophenyl)ethyl]-4-isopropyl-4-methyl-1,3-oxazol-5-one.

Step 2 (Corresponding to the Invention of the Above [5])

Production of 2-(4-Chlorophenyl)-N-[1-methyl-1-isopropyl-2-oxopropyl]propanamide 4.8 g (18 mmol) of 2-[1-(4-chlorophenyl)ethyl]-4-isopropyl-4-methyl-1,3-oxazol-5-one was dissolved in 40 ml of tetrahydrofuran. Thereto was dropwise added, at 5° C., a solution obtained by diluting 20.4 ml of a 1.14 M/liter methyllithium ether solution (23.3 mmol) with 50 ml of tetrahydrofuran. The mixture was kept at 10° C. or below and subjected to a reaction for 1 hour. After the completion of the reaction, ethyl acetate and water were added for phase separation. The separated organic layer was concentrated. The resulting concentrate was subjected to column chromatography to obtain 2.9 g (0.01 mol) (yield=55%) of 2-(4-chlorophenyl)-N-[1-methyl-1-isopropyl-2-oxopropyl]propanamide.

EXAMPLE 2 (Corresponding to the Invention of the Above [5])

Production of 2-(4-Chlorophenyl)-N-[1-methyl-1-isopropyl-2-oxopropyl]propanamide 3.3 g (12.3 mmol) of 2-[1-(4-chlorophenyl)ethyl]-4-isopropyl-4-methyl-1,3-oxazol-5-one was dissolved in 24 ml of tetrahydrofuran. Thereto was added 12.3 ml (37 mmol) of a 3.0 M methylmagnesium chloride tetrahydrofuran solution in three portions. The mixture was subjected to a reaction at 60° C. for 1 hour. The reaction mixture was analyzed by gas chromatography, then confirmed formation of 2-(4-chlorophenyl)-N-[1-methyl-1-isopropyl-2-oxopropyl]propanamide (conversion=40%).

EXAMPLE 3 (Production of the Present Invention Compound of the Above [3])

Production of 2-[2-(4-Chlorophenyl)propanoylamino]-2,3-dimethylbutanoic Acid 0.7 g (2.24 mmol) of methyl 2-[2-(4-chlorophenyl)propanoylamino]-2,3-dimethylbutanoate was dissolved in 20 ml of dimethyl sulfoxide. To the solution was dropwise added, at room temperature with stirring, 5 ml (2.87 mmol) of a 23% sodium hydroxide aqueous solution, and a reaction was allowed to take place at room temperature for 1 hour. Part of the reaction mixture was taken by weighing, acidified (pH=2) with diluted hydrochloric acid, and subjected to extraction with ethyl acetate, after which the extract was analyzed by GC. It was confirmed that the total amount of the methyl 2-[2-(4-chlorophenyl)propanoylamino]-2,3-dimethylbutanoate was converted into 2-(4-chlorophenyl)-N-(1-hydroxycarbonyl-1,2-dimethylpropyl)propionamide. 100 ml of water was added and the mixture was allowed to have a pH of 2 with diluted hydrochloric acid. Extraction was made twice using 100 ml of ethyl acetate. The two organic layers were combined, washed with 50 ml of water, and washed with a saturated aqueous sodium chloride solution. The organic layer obtained was concentrated to obtain 0.5 g (1.7 mmol) (yield=75%) of 2-[2-(4-chlorophenyl)propanoylamino]-2,3-dimethylbutanoic acid.

Industrial Applicability

According to the present invention, there are provided a process for producing a phenylalkanoic acid amide compound having an excellent fungicidal activity, and an intermediate for producing the compound. The present invention has made possible the simple and easy production of a phenylalkanoic acid amide compound having an excellent fungicidal activity.

What is claimed is:

1. A process for producing a phenylalkanoic acid amide represented by the following formula [3]

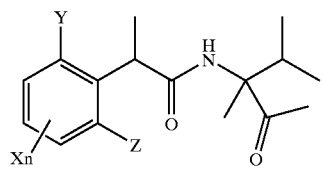

[3]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom), which process comprises reacting a carboxylic acid compound represented by the following formula [1]

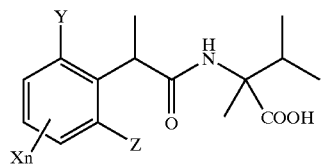

[1]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) with a dehydrating agent to produce an oxazolinone compound represented by the following formula [2]

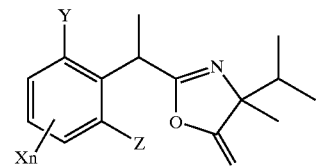

[2]

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) and then reacting the oxazolinone compound with a methylmagnesium halide.

2. An oxazolinone compound represented by the following formula [2]

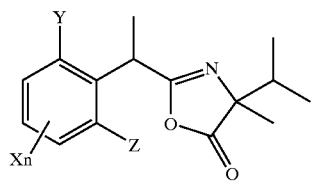

(wherein X is a halogen atom; n is an integer of 1; and Y and Z are each a hydrogen atom).

3. A process for producing a phenylalkanoic acid amide represented by the following formula [3]

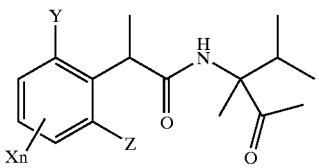

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom), which process comprises reacting. an oxazolinone compound represented by the following general formula [2]

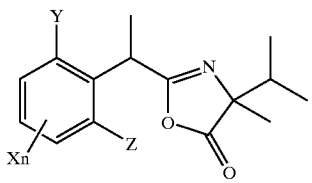

(wherein X is a hydrogen atom, an alkyl group, an alkoxy group, a haloalkyl group or a halogen atom; n is an integer of 1 to 3; when n is 2 or more, a plurality of Xs may be the same or different; and Y and Z are each independently a halogen atom or a hydrogen atom) with a methylmagnesium halide.

4. A process for producing a phenylalkanoic acid amide, according to claim 1, wherein the dehydrating agent is an acid anhydride, a thionyl halide compound, a phosphorus halide compound or a halocarbonic acid ester compound.

5. A process for producing a phenylalkanoic acid amide, according to claim 1, wherein the methylmagnesium halide is methylmagnesium chloride or methylmagnesium bromide.

6. A process for producing a phenylalkanoic acid amide, according to claim 1, wherein the dehydrating agent is an acid anhydride, a thionyl halide compound, a phosphorus halide compound or a halocarbonic acid ester compound and the methylmagnesium halide is methylmagnesium chloride or methylmagnesium bromide.

7. A process for producing a phenylalkanoic acid amide, according to claim 3, wherein the methylmagnesium halide is methylmagnesium chloride or methylmagnesium bromide.

* * * * *